United States Patent [19]

Mansell

[11] 4,028,426

[45] June 7, 1977

[54] REMOVAL OF MONOCHLOROACETYLENE FROM CHLORINATED HYDROCARBONS

[75] Inventor: John Douglas Mansell, Corpus Christi, Tex.

[73] Assignee: PPG Industries, Inc., Pittsburgh, Pa.

[22] Filed: Nov. 18, 1975

[21] Appl. No.: 632,922

[52] U.S. Cl. .................. 260/652 P; 260/654 S
[51] Int. Cl.² .................................. C07C 17/38
[58] Field of Search ....... 260/659 A, 654 A, 654 S, 260/652 P

[56] References Cited

UNITED STATES PATENTS 2,809,221   10/1957   Thomas et al. ............... 260/659 A

*Primary Examiner*—D. Horwitz
*Attorney, Agent, or Firm*—Irwin M. Stein; Roger S. Benjamin

[57] ABSTRACT

Monochloroacetylene occurring as an impurity in 1,1-dichloroethylene is removed by chemical reaction in the presence of an aqueous HCl/cuprous chloride catalyst composition.

8 Claims, No Drawings

REMOVAL OF MONOCHLOROACETYLENE FROM CHLORINATED HYDROCARBONS

BACKGROUND OF THE INVENTION

Monochloroacetylene (MCA) is a toxic, detonable and volatile compound produced as a minor byproduct in the dehydrochlorination of 1,1,2-teichloroethane to form 1,1-dichloroethylene product. The MCA content in the chlorohydrocarbon product is dependent on the type of dehydrochlorination process, for example, thermal dehydrochlorination products typically have MCA levels in excess of 10 p.p.m., whereas alkaline dehydrochlorination products typically have MCA levels in excess of 200 p.p.m.

Distillative techniques have been used to separate the lower boiling MCA from the 1,1-dichloroethylene product but in large scale industrial operations the temporary accumulation of large quantities of MCA and its subsequent disposal constitute a problem. In addition, it is recognized practice to avoid the presence of copper in 1,1-dichloroethylene product processing systems since copper may result in the formation of highly explosive acetylides.

Nieuwland-type catalyst solutions containing copper salts and halogen acids have been used to prepare a variety of chlorinated hydrocarbon derivatives using acetylene as the principal reactant (see U.S. Pat. No. 2,915,565 issued to A. Jacobowsky et al and U.S. Pat. No. 3,197,515 issued to P. Chassaing et al).

THE INVENTION

It has now been discovered that a liquid catalyst composition comprising aqueous haloid acid and cuprous halide will promote the chemical reaction of MCA contained in chlorohydrocarbon products or byproduct streams into innocuous byproducts to give a chlorohydrocarbon product which is free or substantially free of MCA.

DETAILED DESCRIPTION OF THE INVENTION

In accordance with the invention, the MCA contents of normally liquid chlorohydrocarbons may be reduced or even removed by contact with a liquid catalyst composition having as essential constituents a haloid acid and cuprous ion to effect chemical conversion of the MCA to innocuous compounds, most probably dichloroethylenes. The haloid acid is preferably hyrochloric acid but may be hydrobromic acid hydriodic acid. Presence of the cuprous ion is typically provided by a salt notably a cuprous halide such as cuprous chloride, cuprous bromide or cuprous iodide. Cuprous chloride is preferred because it is readily available and is soluble in hydrochloric acid.

The acid content of the liquid catalyst composition should preferably be maintained at a high level for two reasons. First, it insures acidity of the chlorohydrocarbon products thereby preventing the copper component of the catalyst composition from forming hazardous copper acetylides. Second, the haliod acid serves as a reactant since it is theorized to participate in the chemical reaction of MCA, as for example:

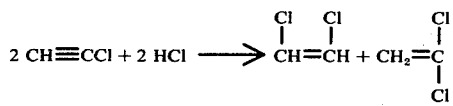

It is desirable to use concentrated commercial haloid acids; specifically, hydrochloric acid containing 36 weight percent HCl, hydrobromic acid containing 48 weight percent HBr or hyroidic acid containing 57 weight percent HI, are useful in preparing the liquid catalyst composition. One or more haloid acids or cuprous halides may be used to form the catalyst composition, for example, hydrochloric acid and hydrobromic acid may be admixed with cuprous iodide and cuprous chloride.

The cuprous halide must be dissolved in the halide acid to provide the cuprous ion necessary to catalyze the reaction of the MCA. High MCA reaction rates are associated with high cuprous in concentration, so that it is advantageous to prepare the catalyst composition saturated with solubilized cuprous halide. It is possible to increase the cuprous ion content of the catalyst composition by including therein such materials as chelating agents, for example, trisodium nitrilotriacetate or salts which provide ions that form soluble complexes, for example, KCl, MaCl, $MgCl_2$, $NH_4Cl$, and $BaCl_2$.

Generally, it is preferred to have the hydrogen halide content above 4 weight percent based on the weight of catalyst composition. The cuprous halide content of the catalyst composition is at least 1 weight percent of its maximum solubility in the catalyst composition. Typical cuprous chloride concentrations are from 2 to 14.5 weight percent of the catalyst composition.

The composition may be preformed by dissolving cuprous halide in haloid acid. The acid content destroyed by reaction with MCA may be replenished by thereafter passing dry hydrogen halide into the catalyst mixture. In addition, in situ formation may be accomplished by feeding separately, or in any combination or sequence; water, hydrogen halide (e.g., HCl, HBr, HI) and solid cuprour halide to the chlorohydrocarbon product containing MCA. Agitation of the mixture will form the haloid acid and solubilize the cuprous salt to form the catalyst composition.

The ratio of catalyst composition to liquid chlorohydrocarbon product may vary within wide limits depending on catalyst strength, catalyst contact time and temperature. In typical practice of the catalyst composition will be 0.1 to 100 volume percent of the chlorohydrocarbon product volume.

Temperatures consistent with maintaining the catalyst composition in liquid form are used. Thus, the liquid catalyst composition is normally maintained at a temperature above 0° C. to below the boiling point of the composition at the pressure of process operation. Normally temperatures between 5° and 80° C. are used in operating the process.

Reactive contact between the catalyst composition and the MCA containing chlorohydrocarbon may be accomplished by a variety of means. For example, the liquid catalyst may be contacted by simply mixing with a liquid media containing MCA. Alternately, gaseous MCA may be fed into the liquid catalyst solution, for example, by passing the gaseous stream of MCA upwardly through a shower of the liquid catalyst, as in a scrubber.

When it is desired to add the catalyst composition directly to the product, the composition of the catalyst may be altered to adjust its density to above or below that of the chlorohydrocarbon sought to be purified by removal of MCA. This adjustment of density permits separation of the purified product as either a bottom or top layer as required by by the nature of the operation. For example, a saturated solution of cuprous chloride in concentrated hydrochloric acid (~36 percent HCl) has a density greater than liquid 1,1-dichloroethylene and may be comveniently phase separated after being contacted with the product by agitation.

The time for process operation is shortened by any factor which will increase contact of the mutually immiscible chlorohydrocarbon product and the catalyst composition, for example, stirring, shaking, counter current flow or use of packed columns. Generally, contact times of one-tenth second to 10 hours will suffice to remove or substantially reduce the MCA. The process may be operated at any convenient pressure but preferably pressures are employed which will encourage retention of the volatile MCA in the apparatus containing the catalyst composition. In most instances, pressures of 1 to 10 atmospheres are suitable.

The removal of the MCA from the chlorohydrocarbon product may be monitored by gas chromatography.

The process of this invention may be used to remove MCA from any product which is unreactive with the catalyst composition. The products which are intended to be purified by the process of this invention are carbon compounds; normally liquid saturated or ethylenically unsaturated chlorohydrocarbons (including carbon tetrachloride). In general, these chloro carbons contain 1 to 3 carbons and typically include 1,2-dichloroethane, 1,1,1-trichloroethane, perchloroethylene, trichloroethylene and tetrachloroethane. The MCA removal process may be conducted as a batch or continuous operation.

A more complete understanding of how the invention may be practiced is seen from the following process description:

1,1,2-trichloroethane is dehydrochlorinated with sodium hydroxide to yield a reaction mixture of unreacted trichloroethane, 1,2-dichloroethylenes, water, 1,1-dichloroethylenes and several hundred p.p.m. of MCA. A first distillation removes the water, MCA and dichloroethylenes as overhead. The overhead fraction of the first distillation is distilled in a second distillation apparatus to provide an overhead stream of water, 1,1-dichloroethylene and MCA. This overhead stream of the second distillation is sent to a third distillation apparatus which retains purified 1,1-dichloroethylene and eliminates as overhead impurities such as MCA and water (in the form of water/1,1-dichloroethylene azeotrope). The third distillation overhead is vented to a heated packed column containing concentrated hydrochloric acid/cuprous chloride catalyst composition. MCA is removed by chemical action at this point in the process. Hydrogen chloride gas is passed into the packed column to assure that reacted hydrochloric acid is continuously replaced. The packed column output is passed to a condenser and hence to water scrubber for removal of contained HCl, then to a phase separator for removal and recycling of the contained chlorohydrocarbons.

EXAMPLE

Samples of 1,1-dichloroethylene produced by alkaline dehydrochlorination of 1,1,2-trichloroethane and containing 3900 parts per million MCA were placed in 340 ml. glass bottles fitted with a rubber septum cap. The bottles were vigorously shaken with catalyst composition under conditions recited in the Table, and thereafter analyzed for their MCA content.

Liquid catalyst compositions having the following formulation were employed:

|  | No. 1 Wt. % | No. 2 Wt. % |
|---|---|---|
| $Cu_2Cl_2$ | 8.4 | 14.5 |
| HCl | 18.84 | 32.5 |
| $H_2O$ | 72.76 | 53.0 |

TABLE

Removal of MCA[1] from 1,1-dichloroethylene

| Sample | Catalyst Composition | Catalyst Volume ml. | Sample Volume ml. | Contact Time Min. | Temperature °C. | MCA After Treatment p.p.m. |
|---|---|---|---|---|---|---|
| 1 | No. 1 | 59.5 | 61 | 60 | 23 | 38 |
| 2 | Control* | 50 | 50 | 30 | 23 | 3900 |
| 3 | No. 2 | 69 | 61 | 30 | 23 | 125 |
| 4 | No. 2 | 69 | 61 | 10 | 45 | 293 |

[1]Initial MCA concentration, 3900 p.p.m.
*20.5 weight percent hydrochloric acid only.

It is apparent that a substantial portion of contained MCA is removed by contact with the HCl—$Cu_2Cl_2$ catalyst composition. A control experiment absent cuprous ion was ineffective in removing MCA.

While the present invention has been described with respect to certain details of specific embodiments, it is not intended that the invention be construed as limited to such details except insofar as they are set forth in the appended claims.

I claim:

1. A method of reducing the monochloroacetylene content of liquid saturated or ethylenically unsaturated chlorohydrocarbons which comprises contacting said chlorohydrocarbons with a liquid catalyst composition comprising cuprous halide and aqueous haloid acid selected from HCl, HBr, HI at a temperature and pressure which mmaintains the catalyst in liquid form.

2. A method according to claim 1 wherein the catalyst composition comprises hydrochloric acid and cuprous chloride.

3. A method according to claim 1 wherein the catalyst composition is contacted with the liquid saturated or ethylenically unsaturated chlorohydrocarbons for a time from one-tenth second to 10 hours.

4. A method according to claim 2 wherein the aqueous catalyst composition consists essentially of above 4 weight percent hydrogen chloride based on the weight of catalyst composition and solubilized cuprous chloride at a concentration of at least one weight percent of its maximum solubility in the catalyst composition.

5. A method according to claim 1 wherein the liquid saturated or ethylenically unsaturated chlorohydrocarbons are contacted with between 0.1 to 100 volume percent of catalyst composition based on the chlorohydrocarbons volume.

6. A method according to claim 4 wherein the catalyst composition has a density greater than 1,1-dichloroethylene.

7. A method of reducing the monochloroacetylene content of liquid saturated or ethylenically unsaturated chlorohydrocarbons by distillation of the monochloroacetylene from said chlorohydrocarbons and subsequent chemical conversion of the monochloroacethylene; wherein the improvement comprises:

contacting the distilled monochloroacetylene with a liquid catalyst composition comprising cuprous halide and aqueous haloid acid selected from HCl, HBr, and HI at a temperature and pressure which maintains the catalyst composition in liquid form.

8. A method according to claim 7 wherein the monochloroacetylene content of a liquid ethylenically unsaturated chlorohydrocarbon consisting of the 1,1-dichloroethylene product prepared by the dehydrochororination of 1,1,2-trichloroethane is reduced.

* * * * *